US011835491B2

(12) United States Patent
Feng et al.

(10) Patent No.: US 11,835,491 B2
(45) Date of Patent: Dec. 5, 2023

(54) DEVICE AND METHOD FOR TESTING BEARING CAPACITY OF GROUPED PILLARS IN INCLINED GOAF UNDER COUPLED BIAXIAL STATIC AND DISTURBANCE STRESSES

(71) Applicant: Taiyuan University of Technology, Shanxi (CN)

(72) Inventors: Guorui Feng, Taiyuan (CN); Tingye Qi, Taiyuan (CN); Jinwen Bai, Taiyuan (CN); Chao Song, Taiyuan (CN); Shuiyun Hou, Taiyuan (CN); Lirong Li, Taiyuan (CN); Yanqun Yang, Taiyuan (CN); Xudong Shi, Taiyuan (CN)

(73) Assignee: Taiyuan University of Technology, Shanxi (CN)

( * ) Notice: Subject to any disclaimer, the term of this patent is extended or adjusted under 35 U.S.C. 154(b) by 171 days.

(21) Appl. No.: 17/586,061

(22) Filed: Jan. 27, 2022

(65) Prior Publication Data

US 2022/0244153 A1 Aug. 4, 2022

(30) Foreign Application Priority Data

Feb. 4, 2021 (CN) .......................... 202110151086.8

(51) Int. Cl.
*G01N 3/10* (2006.01)
*G01N 33/24* (2006.01)
(Continued)

(52) U.S. Cl.
CPC .............. *G01N 3/10* (2013.01); *G01N 33/24* (2013.01); *G01N 3/02* (2013.01); *G01N 3/12* (2013.01);
(Continued)

(58) Field of Classification Search
CPC .. G01N 3/10; G01N 3/12; G01N 3/02; G01N 33/24; G01N 2203/0019; G01N 2203/0048; G01N 2203/0254; G01N 2203/0264
See application file for complete search history.

(56) References Cited

U.S. PATENT DOCUMENTS 7,370,537 B2 * 5/2008 O'Brien ................. G01N 29/14
73/818
8,281,666 B2 * 10/2012 Jevons ..................... G01N 3/24
73/818

(Continued)

*Primary Examiner* — Jonathan M Dunlap
(74) *Attorney, Agent, or Firm* — Harness, Dickey & Pierce, P.L.C.

(57) ABSTRACT

A device and method for testing the bearing capacity of grouped pillars in the inclined goaf under coupled biaxial static and disturbance stresses are provided. Four protection rings are arranged on a base, each protection ring is installed with one machine frame therein, a bottom end of the machine frame is connected with the base and a top end thereof is connected with a transverse frame. Sliding rails are arranged on two sides of the base, side frames are installed on the sliding rails. A vertical force loading device is arranged at a bottom of a workbench, transverse force loading devices are arranged on inner sides of the side frames respectively. A force disturbance device is arranged at the bottom of the transverse frame. An upper slidable clamping seat and an upper pressure disk are arranged above the samples, and a lower slidable clamping seat is arranged below the samples.

18 Claims, 11 Drawing Sheets

(51) Int. Cl.
*G01N 3/12* (2006.01)
*G01N 3/02* (2006.01)
(52) U.S. Cl.
CPC ............. *G01N 2203/0019* (2013.01); *G01N 2203/0048* (2013.01); *G01N 2203/0254* (2013.01); *G01N 2203/0264* (2013.01)

(56) References Cited

U.S. PATENT DOCUMENTS

| 9,983,106 B2* | 5/2018 | Han ...................... G01N 33/24 |
| 10,641,690 B2* | 5/2020 | Brovold ................... G01N 3/20 |
| 2021/0190755 A1* | 6/2021 | Martysevich ............ G01N 3/06 |

* cited by examiner

DEVICE AND METHOD FOR TESTING BEARING CAPACITY OF GROUPED PILLARS IN INCLINED GOAF UNDER COUPLED BIAXIAL STATIC AND DISTURBANCE STRESSES

CROSS REFERENCE TO RELATED APPLICATION

This patent application claims the benefit and priority of Chinese Patent Application No. 202110151086.8 filed on Feb. 4, 2021, the disclosure of which is incorporated by reference herein in its entirety as part of the present application.

TECHNICAL FIELD

The present disclosure relates to a device and method for testing bearing capacity of single-row grouped pillars in the inclined goaf under coupled biaxial static and disturbance stresses, mainly relates to a device and method for synchronously loading multiple coal samples, rock samples, filling body samples, concrete samples, coal-filling samples and rock-filling samples, and belongs to the technical field of rock mechanics tests in mining.

BACKGROUND ART

Due to the undeveloped mining method in the old mining period, a large number of remaining coal pillars are formed in many mines in China and mainly include reamer-pillar coal pillars, room and pillar coal pillars, strip coal pillars, short wall coal pillars, roadway mining coal pillars, warehouse coal pillars, skip mining coal pillars and the like. The coal pillars are densely distributed in space. They are different in shapes and influence one another. The coal pillars are intricate and complex, and different in sizes. They are combined in clusters to form a coal pillar group. Similarly, ore pillar grouped pillars are also formed in a goaf during metal mine mining to bear overburden rock load and guarantee long-term stability of a stope.

Overburden rock movement and surface subsidence can be effectively controlled through filling mining. In recent years, in order to solve the technical problems that filling materials are insufficient in source and high in cost, the technical methods such as partial filling, roadway-side filling, strip filling, pierstud filling, local filling, short wall filling, strip filling, interval filling, pillar-side filling, structure filling, function filling and framework filling are applied and popularized in many mines. For the above filling mining technical methods, filling pillars (concrete pillars) with different sizes/forms are inevitably reserved in the goaf, the filling pillars (concrete pillars) are distributed in the form of grouped pillars and combined to form filling body grouped pillars or concrete grouped pillars. Sometimes, in order to maintain the stability of the remaining coal pillars in the goaf, a pillar-side filling mode is usually adopted. For the pillar-side filling mode, a transverse load is applied to the coal pillar, so that the coal pillar is in a two-way pressed state.

The coal pillar group, the ore pillar group, the filling pillar group and the concrete group are collectively referred to as grouped pillars. The original intention of reserving the grouped pillars in the stope is to bear the load of overburden rock and ensure the long-term stability of the goaf. Long-term stability of stope group pillars is a scientific problem of concern. However, under coupling actions of overburden rock load, disturbance load, mine water erosion, sulfate corrosion, chlorine salt corrosion, natural weathering and the like, the bearing capacity of the grouped pillars in the stope is gradually weakened, which may cause instability of the group pillar system, leading to disasters such as overburden rock collapse and surface subsidence, thereby bring great potential safety hazards to safe and efficient mining of coal resources.

In addition to the static load of the overburden rock load, remaining grouped pillars can also be subjected to strong external disturbance. The disturbance severely threatens the personal safety and the engineering quality. The biaxial bearing capacity of the remaining grouped pillars under the disturbance cannot be researched through the traditional testing machine. The traditional testing machine can only load a single coal pillar, cannot carry out biaxial loading on multiple grouped pillars; therefore, the bearing capacity of the group pillar system to the overburden load after pillar-side filling cannot be researched.

Mutual influence exists among independent individuals of the grouped pillars in the stope, and overburden rock load, disturbance load and the like are not borne by a single pillar body in the stope and are mainly borne by the group pillar system together. If the partial instability damage to one pillar body occurs, the overburden rock load and the disturbance load can be transferred, which further causes the instability failure of the adjacent pillar groups, thereby causing the domino chain instability of the grouped pillars in the stope. Therefore, it is very necessary to test the overall bearing capacity of the group pillar system. At present, it is difficult to perform on-site monitoring of the overall bearing capacity of the grouped pillars in the stope, and only small-size grouped pillar samples in a laboratory can be used for testing. The traditional testing machine can only load a single coal pillar sample, and cannot load grouped pillar samples. In practical engineering, a coal seam usually has a certain inclination angle and is not horizontally distributed. Therefore, it is necessary to research the bearing capacity of the group pillar system at variable angles; however, the biaxial bearing capacity of the group pillar system at variable angles cannot be researched by the traditional testing machine.

In conclusion, it is necessary to provide a device and method for testing the overall bearing capacity of the grouped pillars in the stope, so that the overall bearing capacity of the group pillar system is obtained, the mutual influence relation among group pillar individuals is obtained, thereby laying a foundation for revealing chain instability response characteristics and mechanisms of the grouped pillars in the stope, and providing guidance for research and development of prevention and control technology for the stope group pillar chain instability. The present disclosure provides a device and method for testing bearing capacity of single-row grouped pillars in an inclined goaf under coupled biaxial static and disturbance stresses, focusing on single-row grouped pillars in the inclined goaf.

SUMMARY

The present disclosure provides a device and method for testing bearing capacity of single-row grouped pillars in an inclined goaf under coupled biaxial static and disturbance stresses, particularly relates to a device for synchronously loading a plurality of coal samples, rock samples, filling body samples, concrete samples, coal-filling samples and rock-filling samples; the mutual influence relationship among individuals in the grouped pillars can be obtained through the present disclosure, thereby laying a foundation for revealing chain instability response characteristics and mechanisms of the stope group pillars, and providing guidance for researching and developing chain instability prevention and control technologies of the grouped pillars in the stope.

It is provided a device for testing bearing capacity of grouped pillars in an inclined goaf under coupled biaxial static and disturbance stresses. The device includes a testing machine base, machine frames, a lower pressure disk, an upper pressure disk, an upper slidable clamping seat, a lower slidable clamping seat, a transverse frame, a main loading rod, a main loading oil cylinder, pressure sensors, baffle plates, protection rings, disturbance force sensors, fixed rings, fixed grooves, scale lines, fixed bolts, arc-shaped clamping blocks, fixed rolling shafts, arc-shaped hollow portions, positioning grooves, transverse hydraulic pushing shafts, transverse pressing plates, side pressing plates, side slidable clamping seats, telescopic stand pillars, sliding wheels, sliding rails, fixed blocks and loading devices. The loading devices comprise a vertical force loading device, force disturbance devices and transverse force loading devices.

Four protection rings are arranged on the base, each protection ring is installed with one machine frame therein, a bottom end of the machine frame is connected with the base, a top end of the machine frame is connected with the transverse frame. The sliding rails are arranged on two sides of the base respectively, two side frames are installed on the sliding rails respectively through the telescopic stand pillars and the sliding wheels. The sliding rails are fixed to the base; the vertical force loading device is arranged at a bottom of a workbench and includes a main loading rod, a main loading oil cylinder and a pressure sensor. The transverse force loading devices are arranged on inner sides of the side frames respectively, and each transverse force loading device includes transverse hydraulic pushing shafts, transverse pressing plates, transverse loading oil cylinders and transverse force sensors; each force disturbance device is arranged at a bottom of the transverse frame and includes a disturbance force sensor, a disturbance oil cylinder and a disturbance rod.

The upper slidable clamping seat and the upper pressure disk are arranged above samples, an upper part of the upper slidable clamping seat is connected with the upper pressure disk, the upper pressure disk is connected with the force disturbance device, and the lower slidable clamping seat is arranged below the samples and is connected with the lower pressure disk. The lower pressure disk is fixed on the workbench and is connected with vertical force control device; and the scale lines are arranged on outer edges of the upper slidable clamping seat, the lower slidable clamping seat and the side slidable clamping seats, such that an inclination angle can be accurately adjusted and controlled.

In some embodiments, the grouped pillars include a coal pillar group, an ore pillar group, a filing pillar group, coal pillar-filling pillar combined grouped pillars, ore pillar-filling pillar combined grouped pillars and the like, and the cross sections of the grouped pillars are circular, rectangular, triangular or trapezoidal.

In some embodiments, the device and the method are suitable for the goaf formed by mining a coal seam with the dip angle of −50° to 50°.

In some embodiments, five positioning grooves are formed in the lower pressure disk and used for placing samples, central points of the positioning grooves are positioned on a same straight line, and shapes of the positioning grooves correspond to those of the samples.

In some embodiments, five positioning grooves are formed in the lower pressure disk and used for placing the samples, shapes of the positioning grooves correspond to those of the samples, and central points of the positioning grooves are positioned on a same straight line.

In some embodiments, five fixed grooves are formed on the lower pressure disk and used for placing the baffle plates, such that the samples do not slide off in a rotating process of the device.

In some embodiments, a length, a width and a height of each baffle plate are 300 mm, 5 mm and 90 mm respectively; and lengths and widths of the upper slidable clamping seat and the lower slidable clamping seat are 1000 mm and 400 mm respectively.

In some embodiments, the fixed rings are arranged on outer sides of the upper slidable clamping seat, the lower slidable clamping seat and the side slidable clamping seats respectively. The fixed bolts are arranged in middles of the fixed rings respectively and configured for connecting the upper slidable clamping seat, the lower slidable clamping seat and the side slidable clamping seats with the fixed rings respectively. The arc-shaped clamping blocks are arranged on outer sides of the fixed rings respectively, and the fixed rings are fixedly connected with the fixed blocks of the upper pressure disk, the lower pressure disk and the side pressing plates through the arc-shaped clamping blocks. Furthermore, the fixed rings are arranged between the upper pressure disk and the upper slidable clamping seat, between the lower pressure disk and the lower slidable clamping seat, and between the side pressing plates and the side slidable clamping seats, respectively; the upper pressure disk, the lower pressure disk, the side pressing plates and the fixed rings are connected and fixed through the arc-shaped clamping blocks; a corresponding arc-shaped clamping block between the upper pressure disk and a corresponding fixed ring and another corresponding arc-shaped clamping block between the lower pressure disk and another corresponding fixed ring are of a same structure, an front end and a rear end of each arc-shaped clamping block are provided with one fixed rolling shaft, corresponding fixed blocks are arranged at a bottom of the upper pressure disk and a top of the lower pressure disk respectively, each fixed block is internally provided with an arc-shaped hollow portion for placing a corresponding arc-shaped clamping block, an upper bottom surface and a lower bottom surface of the arc-shaped hollow portion are surfaces provided with the arc-shaped grooves, a central angle corresponding to each arc-shaped groove is 2°, the fixed rolling shafts are positioned between the upper bottom surface and the lower bottom surface of the arc-shaped hollow portion, a rotation angle of the device is adjusted and controlled by rotating the fixed rolling shafts to be matched with the arc-shaped hollow portion, such that a dip angle of the inclined goaf is simulated.

In the present disclosure, five groups of force control devices and ten groups of force control devices are arranged in a vertical direction and a horizontal direction respectively, the five groups of force control devices are arranged in the vertical direction and fixed to the bottom of the workbench, first five groups and second five groups of the ten groups of force control devices are arranged on two sides of the samples in the horizontal direction respectively and fixed to interiors of the side frames. Each force control device includes a pressure sensor, a main loading oil cylinder and a main loading rod, and the main loading oil cylinder controls the main loading rod to apply a load to the upper pressure disk; and each transverse pressing plate is connected with a transverse hydraulic pushing shaft, and is configured for loading different samples at a same speed and at different speeds and simulating a situation in which the samples are subjected to uniform transverse pressure and non-uniform transverse pressure.

The force disturbance device is arranged at a bottom of a cross beam and includes a disturbance force sensor, a disturbance oil cylinder and a disturbance rod. A disturbance load is applied through the disturbance oil cylinder at a top of a testing machine and then applied on the samples through the disturbance rod, and the axial disturbance load in forms of cosine waves, triangular waves and square waves is applied to the samples.

In some embodiments, each transverse pressing plate is connected with a transverse hydraulic pushing shaft, and is configured for loading different samples at a same speed and at different speeds and simulating a situation in which the samples are subjected to uniform transverse pressure and non-uniform transverse pressure.

In some embodiments, the side pressing plates are installed on the sliding rails through the telescopic stand pillars and the sliding wheels, the sliding rails are fixed to the base, heights of the side pressing plates are adjusted through the telescopic stand pillars and positions of the side pressing plates are adjusted through the sliding rails according to actual requirements.

In some embodiments, the device not only can test the biaxial bearing capacity of a horizontal group pillar system, but also can test the biaxial bearing capacity of the group pillar system under variable angles. In the present disclosure, the biaxial bearing capacity of a single coal sample, a single rock sample, a single filling body sample, a single concrete sample, a single coal-filling sample and a single rock-filling sample can be researched, and the biaxial bearing capacity of a plurality of coal, rock, filling body, concrete, coal-filling and rock-filling sample group pillar systems can also be researched.

It is also provided a method for testing bearing capacity of grouped pillars in an inclined goaf under coupled biaxial static and disturbance stresses, by the above device. The testing includes following steps:

comprehensively researching distribution positions, forms and sizes of grouped pillars remaining in the inclined goaf in a to-be-tested range through original geological technical data of a mine in combination with technical means such as supplementary exploration;

determining shapes, sizes and a number of samples to be tested based on information obtained, of the grouped pillars remaining in the inclined goaf;

drilling the samples with appropriate sizes by a core drilling machine specialized for coal rock via a multi-stage variable-speed manual feeding mode, and cutting and grinding the samples to shapes and sizes required for the test by using a coal rock cutting machine;

sequentially installing the samples in the positioning grooves in the lower pressure disk;

placing the baffle plates in the fixed grooves respectively in order to prevent the samples from sliding off in a rotating process of the device; then adjusting positions of the fixed rolling shafts on the arc-shaped hollow interior such that arc-shaped clamping blocks drive the fixed rings, the upper slidable clamping seat, the lower slidable clamping seat and the side slidable clamping seats to rotate and the samples are rotated to a target angle;

resetting force value of each pressure sensor and preloading the samples vertically;

setting a target value to be loaded transversely, and controlling the transverse hydraulic pushing shaft to apply a load to the target value through the transverse hydraulic pump;

setting a loading speed of each vertical hydraulic pushing shaft after transverse loading, and loading the samples;

applying an axial disturbance load through the disturbance rod based on test requirements when an axial load reaches the target value;

continuously applying the axial load after the disturbance load is applied, and stopping loading until the samples are unstable or meets the test requirements; and controlling the vertical hydraulic pushing shaft through the vertical hydraulic pump, controlling the transverse hydraulic pushing shaft through the transverse hydraulic pump for unloading after loading is completed, such that the test is completed.

The present disclosure has the following beneficial effects.

According to the present disclosure, a plurality of coal samples, rock samples, filling body samples, concrete samples, coal-filling samples and rock-filling samples under variable angles can be simultaneously loaded, such that a process in which a plurality of ore pillars can be loaded can be simulated, loading angles of the samples can be continuously changed, thereby researching the biaxial bearing capacity of the group pillar system under different angles.

LIST OF REFERENCE SIGNS

Figure 1:
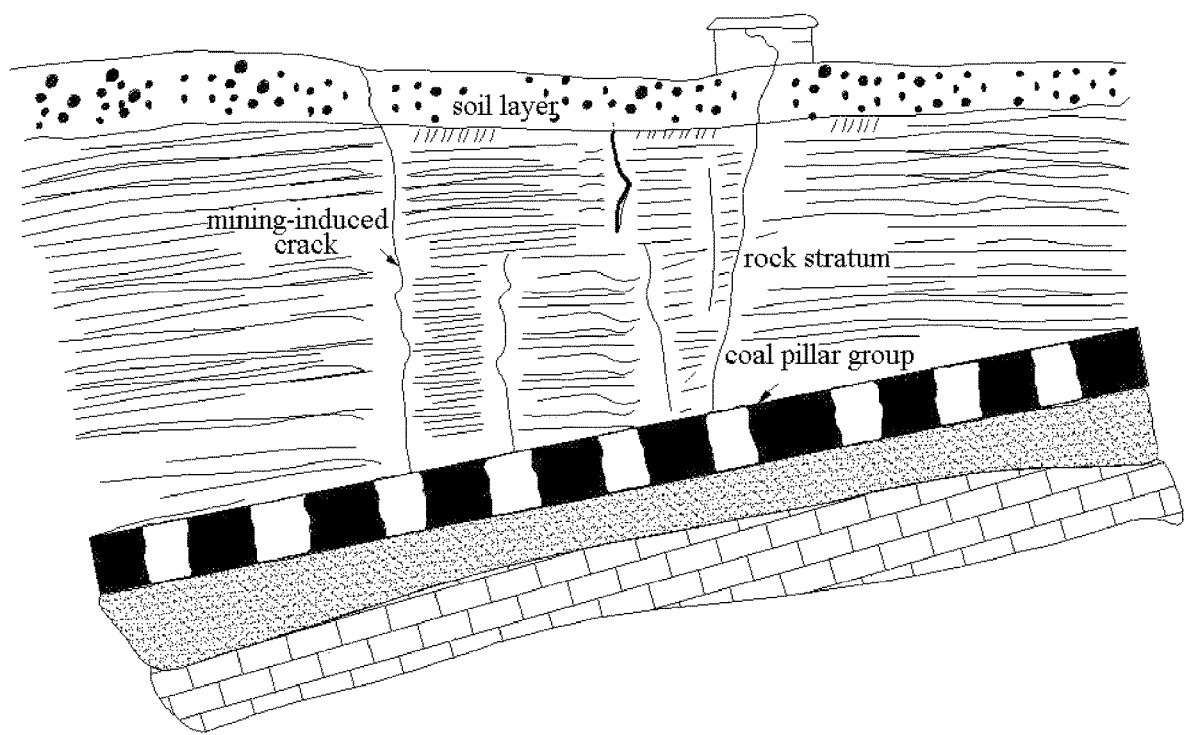
FIG. 1 is a distribution diagram of remaining grouped pillars in an inclined goaf.

1 testing machine base; 2 machine frame; 3 lower pressure disk; 4 upper pressure disk; 5 upper slidable clamping seat; 6 lower slidable clamping seat; 7 transverse frame; 8 main loading rod; 9 main loading oil cylinder; 10 pressure sensor; 11 baffle plate; 12 protection ring; 13 disturbance force sensor; 14 fixed ring; 15 sample; 16 scale line; 17 fixed bolt; 18 arc-shaped clamping block; 19 fixed rolling shaft; 20 arc-shaped hollow portion; 21 positioning groove; 22 transverse hydraulic pushing shaft; 23 transverse pressing plate; 24 side pressing plate; 25 side slidable clamping seat; 26 telescopic stand pillar; 27 sliding wheel; 28 sliding rail; 29 fixed block; 30 disturbance rod; 31 disturbance oil cylinder; 32 transverse loading oil cylinder; and 33 transverse force sensor.

DETAILED DESCRIPTION OF THE EMBODIMENTS

The present disclosure is further illustrated below through embodiments, but not limited to the following embodiments.

Embodiment I

As shown in FIG. 1 to FIG. 12, the present disclosure provides a device for testing bearing capacity of single-row grouped pillars in an inclined goaf under coupled biaxial static and disturbance stresses. The device includes a testing machine base 1, machine frames 2, a lower pressure disk 3, an upper pressure disk 4, an upper slidable clamping seat 5, a lower slidable clamping seat 6, a transverse frame 7, a main loading rod 8, a main loading oil cylinder 9, a pressure sensor 10, baffle plates 11, protection rings 12, a disturbance force sensor 13, fixed rings 14, scale lines 16, fixed bolts 17, arc-shaped clamping block 18, fixed rolling shafts 19, arc-shaped hollow portions 20, positioning grooves 21, transverse hydraulic pushing shafts 22, transverse pressing plates 23, side pressing plates 24, side slidable clamping seats 25, telescopic stand pillars 26, sliding wheels 27, sliding rails 28, fixed blocks 29 and loading devices. The loading devices include a vertical force loading device, a force disturbance device and transverse force loading devices.

Four protection rings 12 are arranged on the testing machine base 1, each protection ring 12 is provided with one machine frame 2 therein, the bottom end of the machine frame 2 is connected with the base. The top end of the machine frame is connected with the transverse frame 7. The sliding rails 28 are arranged on the two sides of the base 1, the side frames are installed on the sliding rails 28 through the telescopic stand pillars 26 and the sliding wheels 27, and the sliding rails 28 are fixed to the testing machine base 1. The vertical force loading device is arranged at the bottom of the workbench and includes a main loading rod 8, a main loading oil cylinder 9 and a pressure sensor 10; the transverse force loading devices are arranged on the inner sides of the side frames respectively, and the transverse force loading device includes transverse hydraulic pushing shafts 22, transverse pressing plates 23, transverse loading oil cylinders 32 and transverse force sensors 33. The force disturbance device is arranged at the bottom of the transverse frame and includes a disturbance force sensor 13, a disturbance oil cylinder 31 and a disturbance rod 30.

The upper slidable clamping seat and the upper pressure disk are arranged above samples, the upper part of the upper slidable clamping seat is connected with the upper pressure disk. The upper pressure disk is connected with the force disturbance device, and the lower slidable clamping seat is arranged at the bottoms of the samples and is connected with the lower pressure disk. The lower pressure disk is fixed on the workbench and is connected with the vertical force control device. The scale lines are arranged on the outer edges of the upper slidable clamping seat, the lower slidable clamping seat and the side slidable clamping seats, so that the inclination angle can be accurately adjusted and controlled.

In some embodiments, the device is suitable for a group pillar system with the inclination angle of −50° to 50°.

In some embodiments, the device is suitable for remaining coal pillars with circular cross sections and also suitable for remaining coal pillars with rectangular cross sections, and more suitable for remaining coal pillars with triangular or trapezoidal cross sections.

Figure 3:
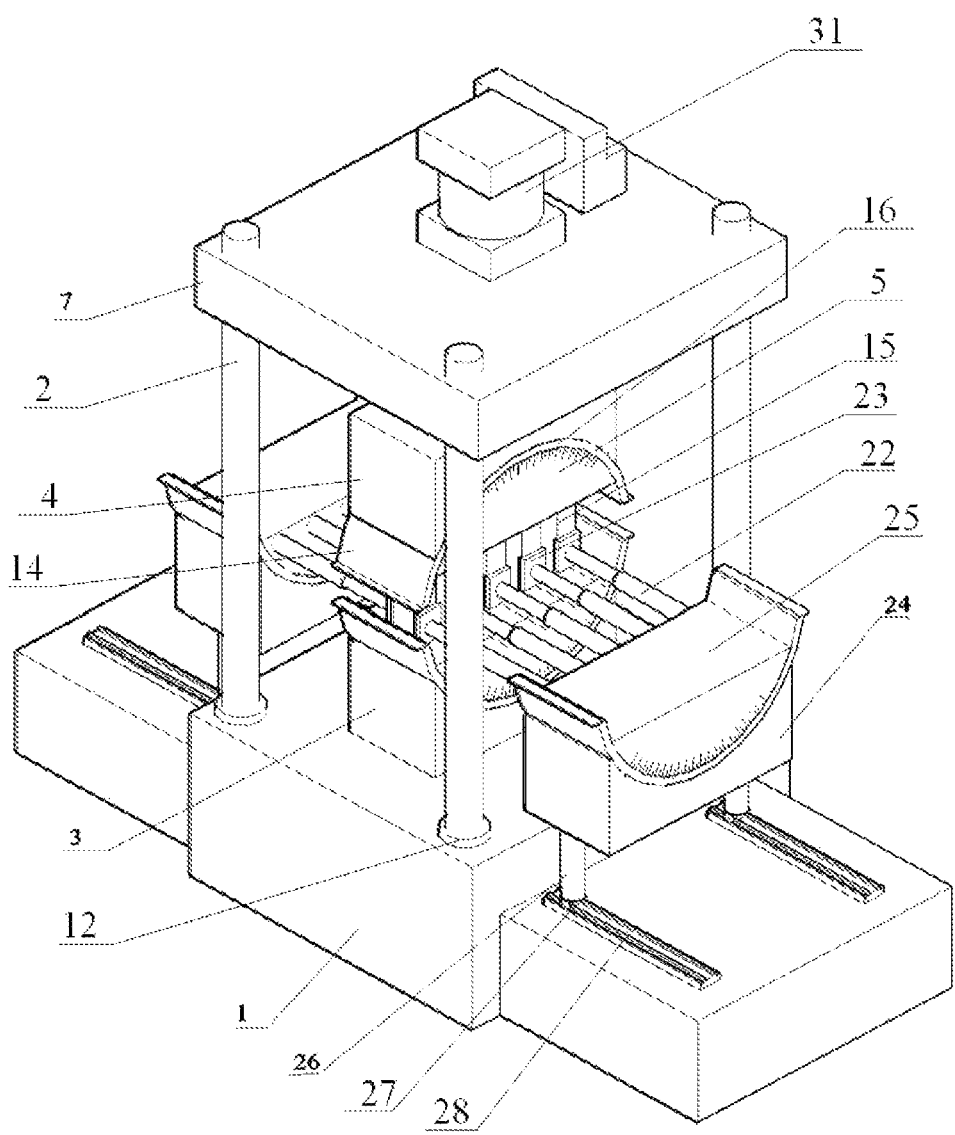
FIG. 3 is a schematic diagram of the present disclosure operated at a horizontal angle.
Figure 4:
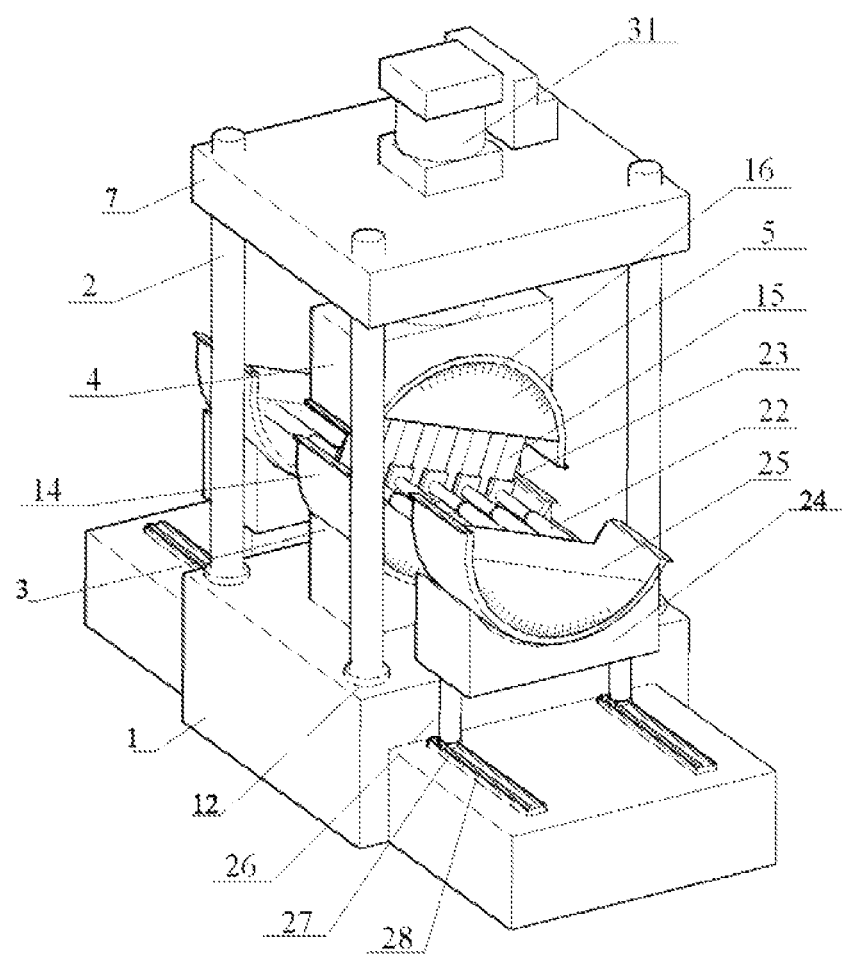
FIG. 4 is a schematic diagram of the present disclosure operated at an inclined angle.

In some embodiments, five positioning grooves 21 are formed in the lower pressure disk 3 and used for placing samples, the central points of the positioning grooves are positioned on the same straight line, and the shapes of the positioning grooves correspond to those of the samples, as shown in FIG. 3.

Figure 2:
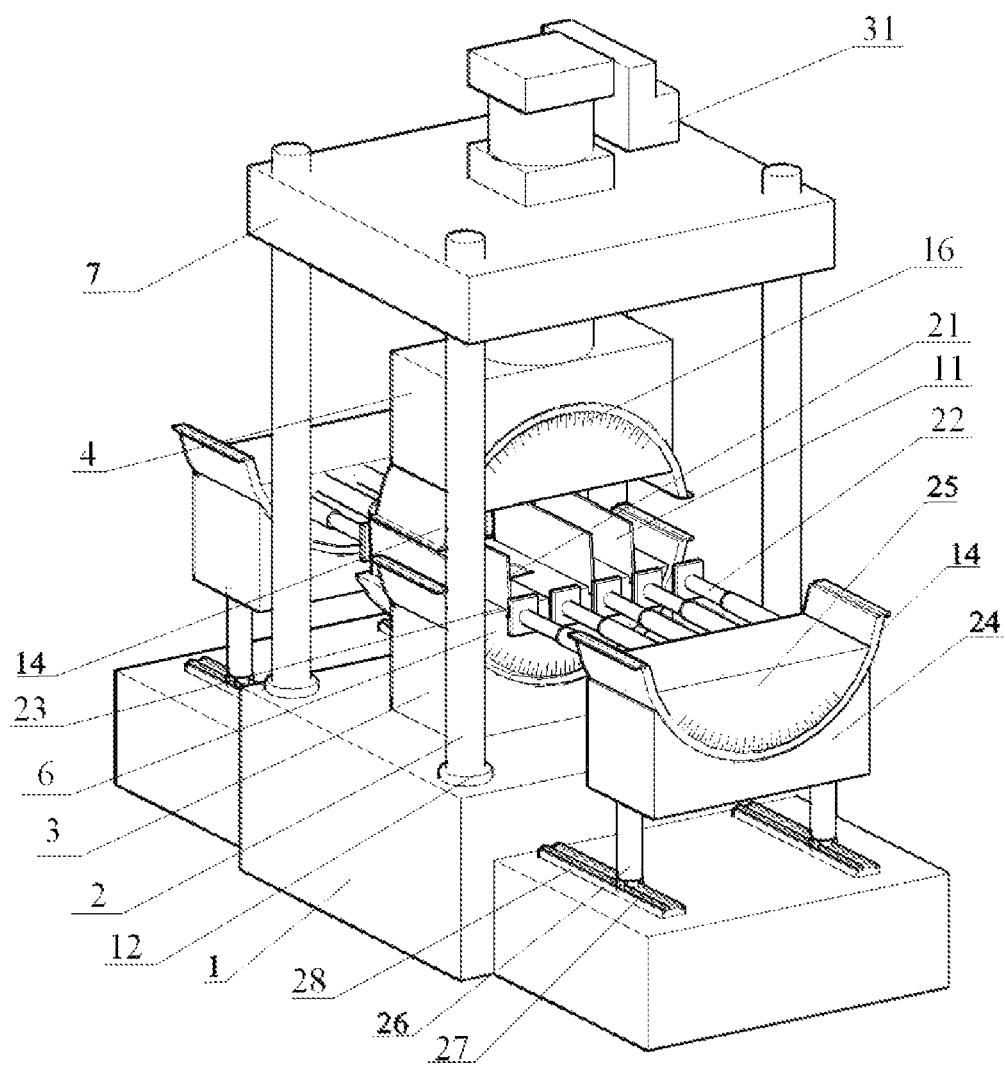
FIG. 2 is a structural schematic diagram according to the present disclosure.

In some embodiments, five fixed grooves are formed in the lower pressure disk 3 and used for placing the baffle plates 11, so that it is guaranteed that the samples do not slide off in the rotating process of the device, as shown in FIG. 2.

The fixed rings are arranged on the outer sides of the upper slidable clamping seat, the lower slidable clamping seat and the side slidable clamping seats, the fixed bolt is arranged in the middle of the fixed ring; the upper slidable clamping seat, the lower slidable clamping seat and the side slidable clamping seats are connected with the fixed rings respectively.

The arc-shaped clamping blocks are arranged on the outer sides of the fixed rings, and the fixed rings are fixedly connected with fixed blocks of the upper pressure disk 3, the lower pressure disk 4 and the side pressing plates 24 through the arc-shaped clamping blocks.

The fixed rings are respectively arranged between the upper pressure disk and the upper slidable clamping seat, between the lower pressure disk and the lower slidable clamping seat, between the side pressing plate and the side slidable clamping seat. The upper pressure disk, the lower pressure disk, the side pressing plates and the fixed rings are connected and fixed through the arc-shaped clamping blocks. The arc-shaped clamping blocks are of the same structure between the upper pressure disk and the fixed ring, between the lower pressure disk and the fixed rings and between the side pressing plates and the fixed rings. The front end and the rear end of the arc-shaped clamping block are each provided with a fixed rolling shaft, the fixed blocks are arranged at the bottom of the upper pressure disk and the top of the lower pressure disk respectively. The fixed block is internally provided with an arc-shaped hollow portion, the arc-shaped hollow portion is used for placing the arc-shaped clamping block. The upper bottom surface and the lower bottom surface of the arc-shaped hollow portion are surfaces provided with arc-shaped grooves. The central angle corresponding to each arc-shaped groove is 2°, the fixed rolling shaft is positioned between the upper bottom surface and the lower bottom surface of the arc-shaped hollow portion. The rotation angle of the device is adjusted and controlled by rotating the fixed rolling shaft to be matched with the arc-shaped hollow portion, thereby simulating the inclination angle of the inclined goaf.

Five groups of force control devices and ten groups of force control devices are arranged in the vertical direction and the horizontal direction respectively. Five groups of force control devices are arranged in the vertical direction and fixed to the bottom of the workbench. Each five groups of force control devices are arranged on the two sides of the samples in the horizontal direction respectively and fixed to the interiors of the side frames. The force control device includes a pressure sensor, a main loading oil cylinder and a main loading rod. The main loading oil cylinder controls the main loading rod to apply a load to the upper pressure disk. Each transverse pressing plate 23 is connected with one transverse hydraulic pushing shaft 22, which can load different samples at the same speed and at different speeds, thereby simulating the situation in which the samples are subjected to uniform transverse pressure and non-uniform transverse pressure.

The device includes the force disturbance device. The force disturbance device includes a disturbance force sensor 13, a disturbance oil cylinder 31 and a disturbance rod 30, and axial disturbance loads in the forms of cosine waves, triangular waves and square waves are applied to the samples.

In some embodiments, the length, the width and the height of the baffle plate 11 are 300 mm, 5 mm and 90 mm respectively; and the lengths and the widths of the upper sliding clamping seat 5 and the lower sliding clamping seat 6 are 1000 mm and 400 mm respectively.

In some embodiments, the scale lines 16 are arranged on the upper slidable clamping seat 5, the lower slidable clamping seat 6 and the side slidable clamping seats 25, so that the inclination angle can be accurately adjusted and controlled, as shown in FIG. 2.

Figure 5:
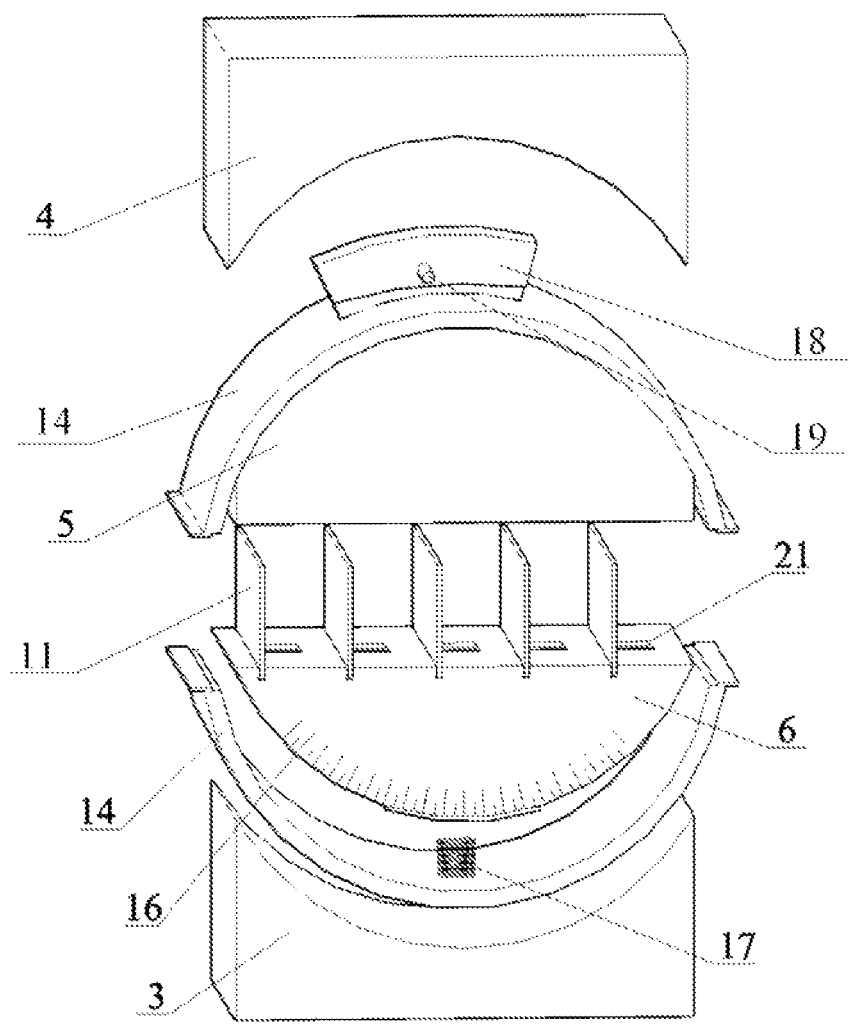
FIG. 5 is an exploded schematic diagram of a loading device in the present disclosure.

Preferably, the upper pressure disk 3, the lower pressure disk 4 and the fixed rings 14 are fixedly connected through the arc-shaped clamping blocks 18, and the fixed rings 14 are connected with the upper slidable clamping seat 5 and the lower slidable clamping seat 6 through the fixed bolts 17, as shown in FIG. 5.

Figure 6:
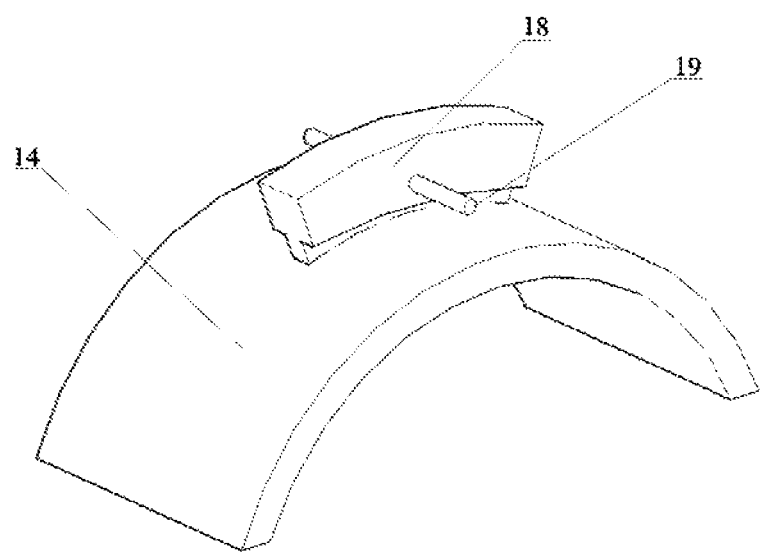
FIG. 6 is a structural schematic diagram of a fixed ring in the present disclosure.
Figure 7:
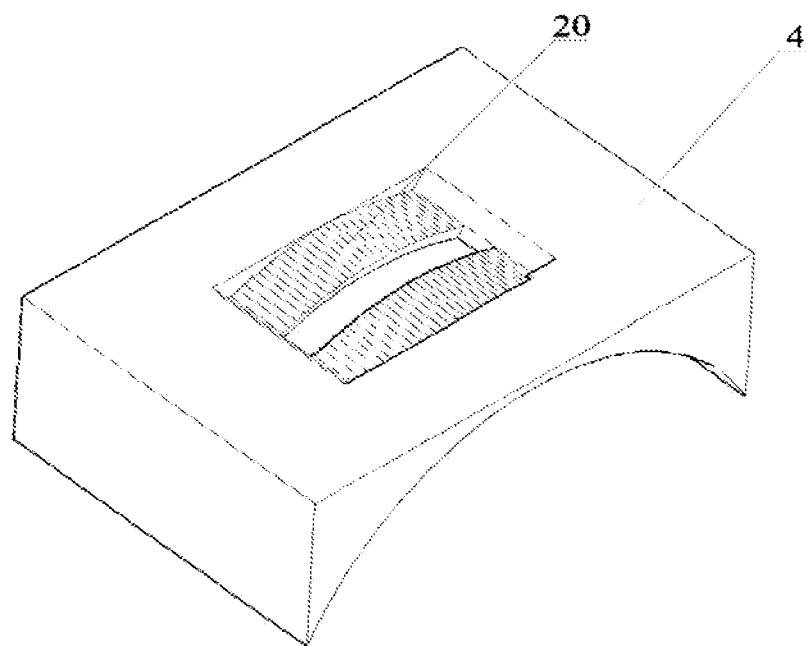
FIG. 7 is a structural schematic diagram of an interior of an upper pressure disk in the present disclosure.

In some embodiments, two fixed rolling shafts 19 are arranged on the arc-shaped clamping block 18, arc-shaped grooves are formed in the pressure disk, the interval between every two adjacent arc-shaped grooves is 2°, and the rotation angle of the device is adjusted and controlled through cooperation of the fixed rolling shafts 19 and the arc-shaped grooves, as shown in FIG. 6 and FIG. 7.

Figure 8:
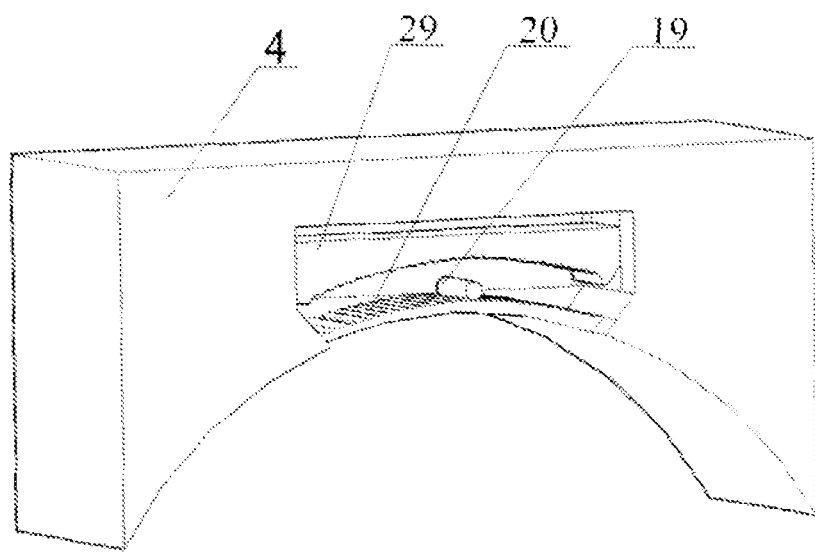
FIG. 8 shows a connection relationship between an arc-shaped hollow portion of an upper fixed block and fixed rolling shafts in the present disclosure.
Figure 9:
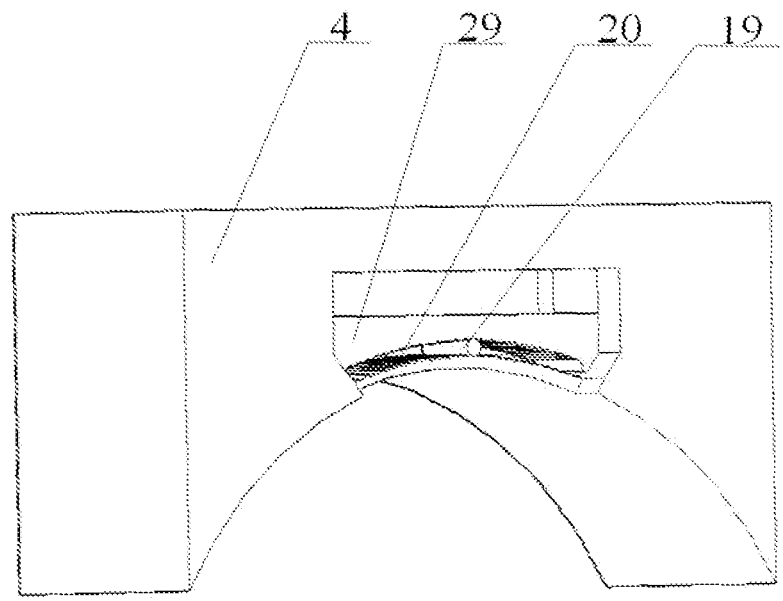
FIG. 9 is a schematic diagram showing engagement between the arc-shaped hollow portion of the upper fixed block and the fixed rolling shafts in the present disclosure.
Figure 10:
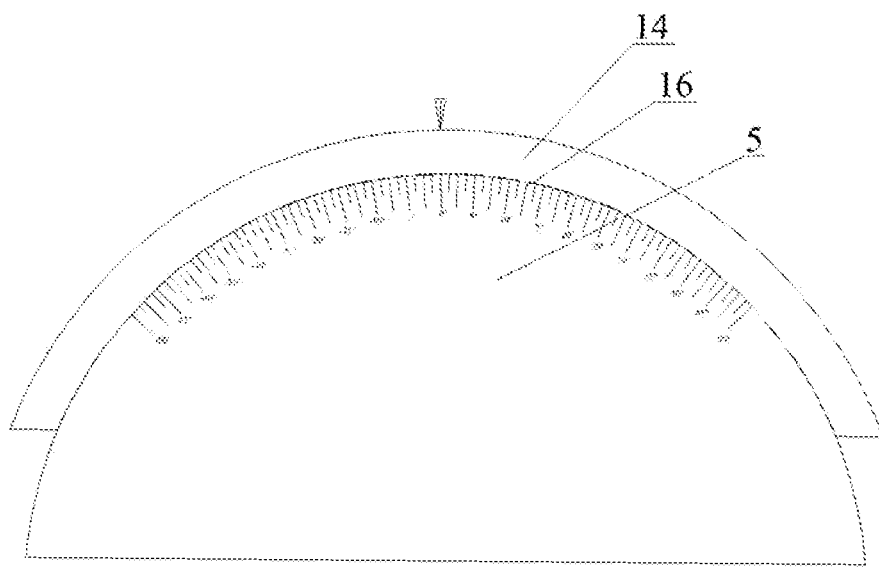
FIG. 10 is a schematic diagram of scales on an upper slidable clamping seat in the present disclosure.

In some embodiments, the fixed blocks are arranged in the upper pressure disk and the lower pressure disk and engaged with the arc-shaped hollow portion to clamp the fixed rolling shafts 19, so that the device is fixed after being rotated, as shown in FIG. 8 and FIG. 9.

In some embodiments, each transverse pressing plate 23 is connected with one transverse hydraulic pushing shaft 22, which can load different samples at the same speed and at different speeds, thereby simulating the situation in which the samples are subjected to uniform transverse pressure and non-uniform transverse pressure, as shown in FIG. 3.

Figure 11:
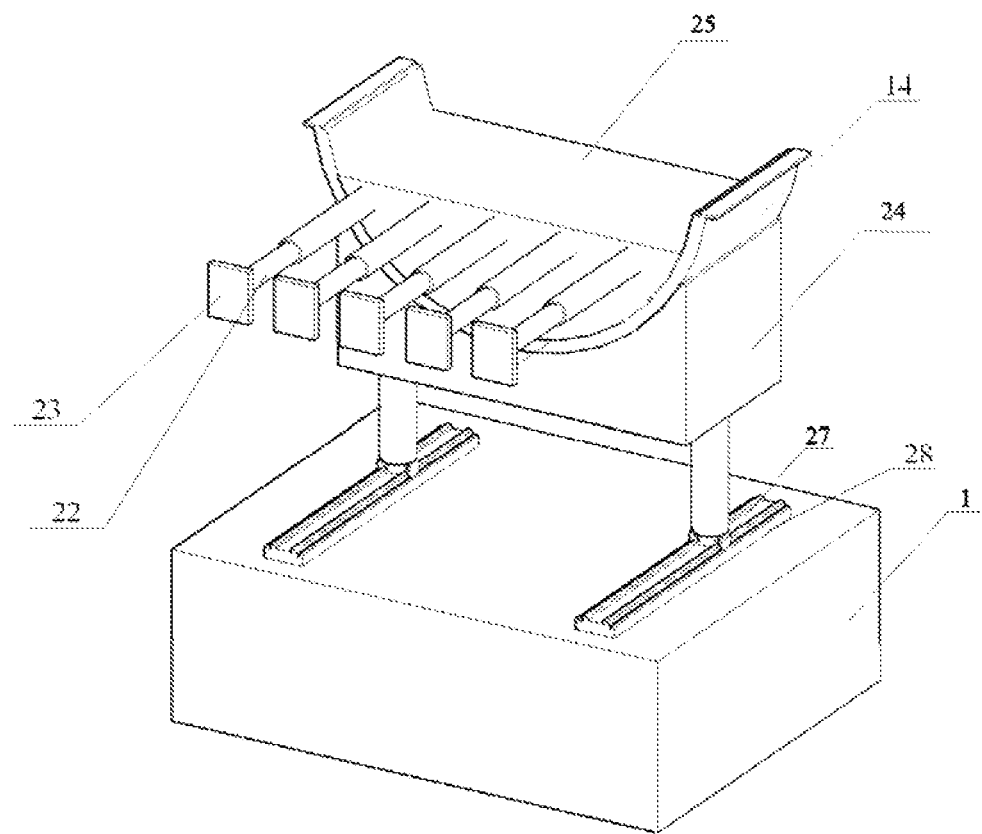
FIG. 11 is a schematic diagram showing a transverse loading device of the present disclosure.
Figure 12:
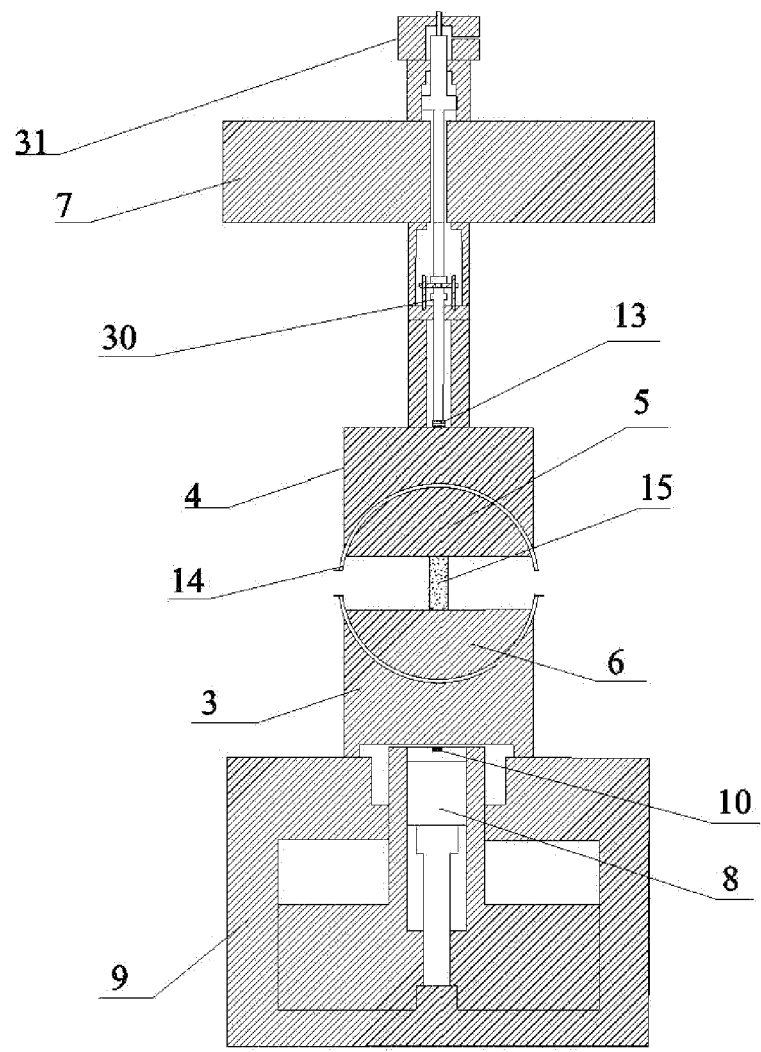
FIG. 12 is a section view of the loading device in the present disclosure.
Figure 13:
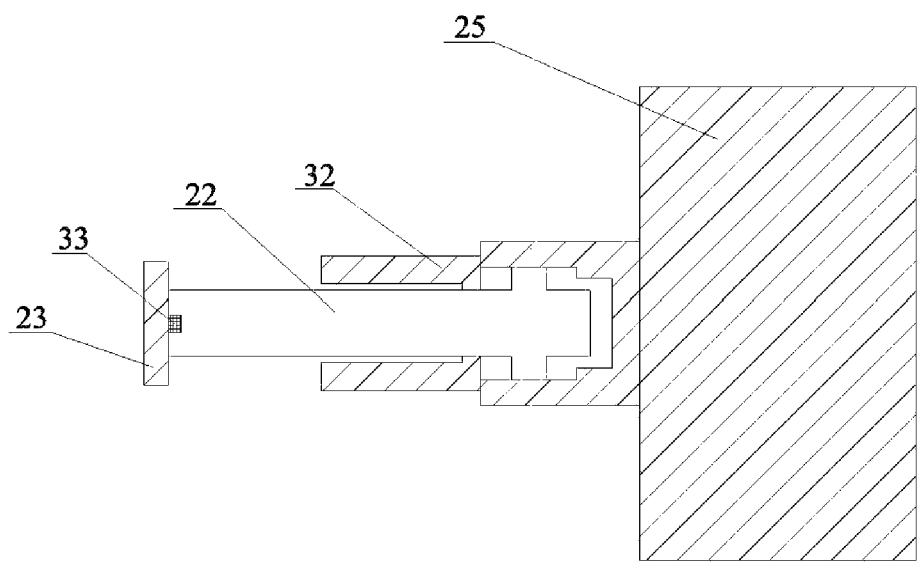
FIG. 13 is a schematic diagram of the transverse loading device in the present disclosure.

In some embodiments, the side pressing plates 24 are installed on the sliding rails 28 through the telescopic stand pillars 26 and the sliding wheels 27, the sliding rails 28 are fixed to the base 1, the heights of the side pressing plates 24 can be adjusted through the telescopic stand pillars 26 according to actual requirements, and the positions of the side pressing plates 24 can be adjusted through the sliding rails 28, as shown in FIG. 11.

In some embodiments, the device not only can test the biaxial bearing capacity of a group pillar system at a horizontal angle, but also can test the biaxial bearing capacity of the group pillar system at variable angles. The biaxial bearing capacity of a single coal sample, a single rock sample, a single filling body sample can be researched, and the biaxial bearing capacity of a plurality of group pillar systems for coal, rock, filling body can also be researched.

In some embodiments, the operating steps of the device includes the following steps:

Step 1, comprehensively researching distribution positions, forms and sizes of grouped pillars remaining in an inclined goaf in a to-be-tested range, by utilizing original geological technical data of a mine and combining technical means such as supplementary exploration;

Step 2, determining shapes, sizes and the number of samples to be tested based on the information, of the grouped pillars remaining in the inclined goaf, obtained in Step 1;

Step 3, drilling the samples with appropriate sizes by a core drilling machine specialized for coal rock through a multi-stage variable-speed manual feeding mode, and cutting and grinding the samples to shapes and sizes required for the test by a coal rock cutting machine;

Step 4, sequentially installing the samples in the positioning grooves in the lower pressure disk;

Step 5, in order to prevent the samples from sliding off in the rotating process of the device, firstly placing baffle plates in fixed grooves; then adjusting the positions of fixed rolling shafts on the arc-shaped grooves, so that arc-shaped clamping blocks drive the fixed rings, the upper slidable clamping seat, the lower slidable clamping seat and the side slidable clamping seats to rotate, and then the loaded samples can be rotated to a target angle;

Step 6, resetting the force value of each pressure sensor, and preloading the samples vertically;

Step 7, setting a target value to be loaded transversely, and controlling a transverse hydraulic pushing shaft through a transverse hydraulic pump to load to a target value;

Step 8, after transverse loading is completed, setting the loading speed of each vertical hydraulic pushing shaft respectively, and loading the samples;

Step 9, when axial loading reaches the target value, applying an axial disturbance load by utilizing a disturbance rod according to test requirements;

Step 10, continuously applying an axial load after the disturbance load is applied, and stopping loading until the samples are unstable or meets the test requirements; and Step 11, after loading is completed, controlling the vertical hydraulic pushing shaft through a vertical hydraulic pump, controlling the transverse hydraulic pushing shaft through the transverse hydraulic pump for unloading, so that the test is completed.

It should be noted that the present disclosure is not limited to the above-described embodiments. The above-described embodiments of the present disclosure may be simply modified in accordance with the essence of the present disclosure, which all fall within the scope of the technical scheme of the present disclosure.

What is claimed is:

1. A device for testing bearing capacity of grouped pillars in an inclined goaf under coupled biaxial static and disturbance stresses, comprising a testing machine base, machine frames, a lower pressure disk, an upper pressure disk, an upper slidable clamping seat, a lower slidable clamping seat, a transverse frame, baffle plates, protection rings, fixed rings, scale lines, fixed bolts, arc-shaped clamping blocks, fixed rolling shafts, arc-shaped hollow portions, positioning grooves, side pressing plates, side slidable clamping seats, telescopic stand pillars, sliding wheels, sliding rails, fixed blocks and loading devices, wherein the loading devices comprise a vertical force loading device, force disturbance devices and transverse force loading devices;

four protection rings are arranged on the base, each protection ring is installed with one machine frame therein, a bottom end of the machine frame is connected with the base, a top end of the machine frame is connected with the transverse frame, the sliding rails are arranged on two sides of the base respectively, two side frames are installed on the sliding rails respectively through the telescopic stand pillars and the sliding wheels, and the sliding rails are fixed to the base; the vertical force loading device is arranged at a bottom of a workbench and comprises a main loading rod, a main loading oil cylinder and a pressure sensor; the transverse force loading devices are arranged on inner sides of the side frames respectively, and each transverse force loading device comprises transverse hydraulic pushing shafts, transverse pressing plates, transverse loading oil cylinders and transverse force sensors; each force disturbance device is arranged at a bottom of the transverse frame and comprises a disturbance force sensor, a disturbance oil cylinder and a disturbance rod;

the upper slidable clamping seat and the upper pressure disk are arranged above samples, an upper part of the upper slidable clamping seat is connected with the upper pressure disk, the upper pressure disk is connected with the force disturbance device, and the lower slidable clamping seat is arranged below the samples and is connected with the lower pressure disk; the lower pressure disk is fixed on the workbench and is connected with a vertical force control device; and the scale lines are arranged on outer edges of the upper slidable clamping seat, the lower slidable clamping seat and the side slidable clamping seats, so that an inclination angle can be accurately adjusted and controlled.

2. The device according to claim 1, wherein the goaf is formed by mining a coal seam with a dip angle of −50° to 50°; the grouped pillars comprise one of a coal pillar group, an ore pillar group, a filling pillar group, a concrete pillar group, a coal pillar-filling pillar combined pillar group, an ore pillar-filling pillar combined pillar group and a coal pillar-concrete pillar combined pillar group; and a cross section of the group pillar is circular, rectangular, triangular or trapezoidal.

3. The device according to claim 1, wherein five positioning grooves are formed in the lower pressure disk and used for placing the samples, shapes of the positioning grooves correspond to those of the samples, and central points of the positioning grooves are positioned on a same straight line; central points of the transverse pressing plates are positioned on a same straight line; and five fixed grooves are formed on the lower pressure disk and used for placing the baffle plates, such that the samples do not slide off in a rotating process of the device.

4. The device according to claim 1, wherein the side pressing plates are installed on the sliding rails through the telescopic stand pillars and the sliding wheels, the sliding rails are fixed to the base, heights of the side pressing plates are adjusted through the telescopic stand pillars and positions of the side pressing plates are adjusted through the sliding rails according to actual requirements.

5. The device according to claim 1, wherein the fixed rings are arranged on outer sides of the upper slidable clamping seat, the lower slidable clamping seat and the side slidable clamping seats respectively, the fixed bolts are arranged in middles of the fixed rings respectively and configured for connecting the upper slidable clamping seat, the lower slidable clamping seat and the side slidable clamping seats to the fixed rings respectively; and the arc-shaped clamping blocks are arranged on outer sides of the fixed rings respectively, and the fixed rings are fixedly connected with the fixed blocks of the upper pressure disk, the lower pressure disk and the side pressing plates through the arc-shaped clamping blocks.

6. The device according to claim 5, wherein the fixed rings are arranged between the upper pressure disk and the upper slidable clamping seat, between the lower pressure disk and the lower slidable clamping seat, and between the side pressing plates and the side slidable clamping seats, respectively; the arc-shaped clamping blocks are configured to connect the upper pressure disk, the lower pressure disk and the side pressing plates to the fixed rings; a corresponding arc-shaped clamping block between the upper pressure disk and a corresponding fixed ring and another corresponding arc-shaped clamping block between the lower pressure disk and another corresponding fixed ring are of a same structure, an front end and a rear end of each arc-shaped clamping block are provided with one fixed rolling shaft, the fixed blocks are arranged at a bottom of the upper pressure disk and a top of the lower pressure disk respectively, each fixed block is internally provided with an arc-shaped hollow portion for placing a corresponding arc-shaped clamping block, an upper bottom surface and a lower bottom surface of the arc-shaped hollow portion are surfaces provided with arc-shaped grooves, a central angle corresponding to each arc-shaped groove is 2°, the fixed rolling shafts are positioned between the upper bottom surface and the lower bottom surface of the arc-shaped hollow portion, a rotation angle of the device is adjusted and controlled by rotating the fixed rolling shafts to be matched with the arc-shaped hollow portion, such that a dip angle of the inclined goaf is simulated.

7. The device according to claim 1, wherein five groups of force control devices and ten groups of force control devices are arranged in a vertical direction and a horizontal direction respectively, the five groups of force control devices are arranged in the vertical direction and fixed to the bottom of the workbench, first five groups and second five groups of the ten groups of force control devices are arranged on two sides of the samples in the horizontal direction respectively and fixed to interiors of the side frames, each force control device comprises a pressure sensor, a main loading oil cylinder and a main loading rod, and the main loading oil cylinder controls the main loading rod to apply a load to the upper pressure disk; and each transverse pressing plate is connected with a transverse hydraulic pushing shaft, and is configured for loading different samples at a same speed and at different speeds and simulating a situation in which the samples are subjected to uniform transverse pressure and non-uniform transverse pressure.

8. The device according to claim 1, wherein the force disturbance device comprises a disturbance force sensor, a disturbance oil cylinder and a disturbance rod, a disturbance load is applied through the disturbance oil cylinder at a top of a testing machine and then applied on the samples through the disturbance rod, and an axial disturbance load in forms of cosine waves, triangular waves and square waves is applied to the samples.

9. The device according to claim 1, wherein a length, a width and a height of each baffle plate are 300 mm, 5 mm and 90 mm respectively; and lengths and widths of the upper slidable clamping seat and the lower slidable clamping seat are 1000 mm and 400 mm respectively.

10. A method for testing bearing capacity of grouped pillars in an inclined goaf under coupled biaxial static and disturbance stresses, adopting a device for testing bearing capacity of grouped pillars in an inclined goaf under coupled biaxial static and disturbance stresses, wherein the device comprises a testing machine base, machine frames, a lower pressure disk, an upper pressure disk, an upper slidable clamping seat, a lower slidable clamping seat, a transverse frame, baffle plates, protection rings, fixed rings, scale lines, fixed bolts, arc-shaped clamping blocks, fixed rolling shafts, arc-shaped hollow portions, positioning grooves, side pressing plates, side slidable clamping seats, telescopic stand pillars, sliding wheels, sliding rails, fixed blocks and loading devices, wherein the loading devices comprise a vertical force loading device, force disturbance devices and transverse force loading devices;

four protection rings are arranged on the base, each protection ring is installed with one machine frame therein, a bottom end of the machine frame is connected with the base, a top end of the machine frame is connected with the transverse frame, the sliding rails are arranged on two sides of the base respectively, two side frames are installed on the sliding rails respectively through the telescopic stand pillars and the sliding wheels, and the sliding rails are fixed to the base; the vertical force loading device is arranged at a bottom of a workbench and comprises a main loading rod, a main loading oil cylinder and a pressure sensor; the transverse force loading devices are arranged on inner sides of the side frames respectively, and each transverse force loading device comprises transverse hydraulic pushing shafts, transverse pressing plates, transverse loading oil cylinders and transverse force sensors; each force disturbance device is arranged at a bottom of the transverse frame and comprises a disturbance force sensor, a disturbance oil cylinder and a disturbance rod;

the upper slidable clamping seat and the upper pressure disk are arranged above samples, an upper part of the upper slidable clamping seat is connected with the upper pressure disk, the upper pressure disk is connected with the force disturbance device, and the lower slidable clamping seat is arranged below the samples and is connected with the lower pressure disk; the lower pressure disk is fixed on the workbench and is connected with a vertical force control device; and the scale lines are arranged on outer edges of the upper slidable clamping seat, the lower slidable clamping seat and the side slidable clamping seats, so that an inclination angle can be accurately adjusted and controlled;

wherein the method comprising following steps:

comprehensively researching distribution positions, forms and sizes of grouped pillars remaining in the inclined goaf in a to-be-tested range through original geological technical data of a mine in combination with technical means such as supplementary exploration;

determining shapes, sizes and a number of samples to be tested based on information obtained, of the grouped pillars remaining in the inclined goaf;

drilling the samples with appropriate sizes by a core drilling machine specialized for coal rock via a multistage variable-speed manual feeding mode, and cutting and grinding the samples to shapes and sizes required for the test by using a coal rock cutting machine;

sequentially installing the samples in the positioning grooves in the lower pressure disk;

placing the baffle plates in the fixed grooves respectively in order to prevent the samples from sliding off in a rotating process of the device; then adjusting positions of the fixed rolling shafts on the arc-shaped hollow portion such that arc-shaped clamping blocks drive the fixed rings, the upper slidable clamping seat, the lower slidable clamping seat and the side slidable clamping seats to rotate and the samples are rotated to a target angle;

resetting a force value of each pressure sensor and preloading the samples vertically;

setting a target value to be loaded transversely, and controlling the transverse hydraulic pushing shaft to apply a load to the target value through the transverse hydraulic pump;

setting a loading speed of each vertical hydraulic pushing shaft after transverse loading, and loading the samples;

applying an axial disturbance load through the disturbance rod based on test requirements when an axial load reaches the target value;

continuously applying the axial load after the disturbance load is applied, and stopping loading until the samples are unstable or meets the test requirements; and controlling the vertical hydraulic pushing shaft through the vertical hydraulic pump, controlling the transverse hydraulic pushing shaft through the transverse hydraulic pump for unloading after loading is completed, such that the test is completed.

11. The method according to claim 10, wherein the goaf is formed by mining a coal seam with a dip angle of −50° to 50°; the grouped pillars comprise one of a coal pillar group, an ore pillar group, a filling pillar group, a concrete pillar group, a coal pillar-filling pillar combined pillar group, an ore pillar-filling pillar combined pillar group and a coal pillar-concrete pillar combined pillar group; and a cross section of the group pillar is circular, rectangular, triangular or trapezoidal.

12. The method according to claim 10, wherein five positioning grooves are formed in the lower pressure disk and used for placing the samples, shapes of the positioning grooves correspond to those of the samples, and central points of the positioning grooves are positioned on a same straight line; central points of the transverse pressing plates are positioned on a same straight line; and five fixed grooves are formed on the lower pressure disk and used for placing the baffle plates, such that the samples do not slide off in a rotating process of the device.

13. The method according to claim 10, wherein the side pressing plates are installed on the sliding rails through the telescopic stand pillars and the sliding wheels, the sliding rails are fixed to the base, heights of the side pressing plates are adjusted through the telescopic stand pillars and positions of the side pressing plates are adjusted through the sliding rails according to actual requirements.

14. The method according to claim 10, wherein the fixed rings are arranged on outer sides of the upper slidable clamping seat, the lower slidable clamping seat and the side slidable clamping seats respectively, the fixed bolts are arranged in middles of the fixed rings respectively and configured for connecting the upper slidable clamping seat, the lower slidable clamping seat and the side slidable clamping seats to the fixed rings respectively; and the arc-shaped clamping blocks are arranged on outer sides of the fixed rings respectively, and the fixed rings are fixedly connected with the fixed blocks of the upper pressure disk, the lower pressure disk and the side pressing plates through the arc-shaped clamping blocks.

15. The method according to claim 14, wherein the fixed rings are arranged between the upper pressure disk and the upper slidable clamping seat, between the lower pressure disk and the lower slidable clamping seat, and between the side pressing plates and the side slidable clamping seats, respectively; the arc-shaped clamping blocks are configured to connect the upper pressure disk, the lower pressure disk and the side pressing plates to the fixed rings; a corresponding arc-shaped clamping block between the upper pressure disk and a corresponding fixed ring and another corresponding arc-shaped clamping block between the lower pressure disk and another corresponding fixed ring are of a same structure, an front end and a rear end of each arc-shaped clamping block are provided with one fixed rolling shaft, the fixed blocks are arranged at a bottom of the upper pressure disk and a top of the lower pressure disk respectively, each fixed block is internally provided with an arc-shaped hollow portion for placing a corresponding arc-shaped clamping block, an upper bottom surface and a lower bottom surface of the arc-shaped hollow portion are surfaces provided with arc-shaped grooves, a central angle corresponding to each arc-shaped groove is 2°, the fixed rolling shafts are positioned between the upper bottom surface and the lower bottom surface of the arc-shaped hollow portion, a rotation angle of the device is adjusted and controlled by rotating the fixed rolling shafts to be matched with the arc-shaped hollow portion, such that a dip angle of the inclined goaf is simulated.

16. The method according to claim 10, wherein five groups of force control devices and ten groups of force control devices are arranged in a vertical direction and a horizontal direction respectively, the five groups of force control devices are arranged in the vertical direction and fixed to the bottom of the workbench, first five groups and second five groups of the ten groups of force control devices are arranged on two sides of the samples in the horizontal direction respectively and fixed to interiors of the side frames, each force control device comprises a pressure sensor, a main loading oil cylinder and a main loading rod, and the main loading oil cylinder controls the main loading rod to apply a load to the upper pressure disk; and each transverse pressing plate is connected with a transverse hydraulic pushing shaft, and is configured for loading different samples at a same speed and at different speeds and simulating a situation in which the samples are subjected to uniform transverse pressure and non-uniform transverse pressure.

17. The method according to claim 10, wherein the force disturbance device comprises a disturbance force sensor, a disturbance oil cylinder and a disturbance rod, a disturbance load is applied through the disturbance oil cylinder at a top of a testing machine and then applied on the samples through the disturbance rod, and an axial disturbance load in forms of cosine waves, triangular waves and square waves is applied to the samples.

18. The method according to claim 10, wherein a length, a width and a height of each baffle plate are 300 mm, 5 mm and 90 mm respectively; and lengths and widths of the upper slidable clamping seat and the lower slidable clamping seat are 1000 mm and 400 mm respectively.

* * * * *